United States Patent [19]
Phillion et al.

[11] Patent Number: 5,994,270
[45] Date of Patent: *Nov. 30, 1999

[54] FUNGICIDES FOR THE CONTROL OF TAKE-ALL DISEASE OF PLANTS

[75] Inventors: Dennis Paul Phillion, St. Charles; Matthew James Graneto, St. Louis, both of Mo.; John Kennedy Pratt, Kenosha, Wis.; Sai Chi Wong, Chesterfield, Mo.

[73] Assignee: Monsanto Company, St. Louis, Mo.

[*] Notice: This patent issued on a continued prosecution application filed under 37 CFR 1.53(d), and is subject to the twenty year patent term provisions of 35 U.S.C. 154(a)(2).

[21] Appl. No.: 08/712,139

[22] Filed: Sep. 11, 1996

Related U.S. Application Data

[63] Continuation of application No. 08/204,610, Mar. 8, 1994, abandoned, which is a continuation-in-part of application No. 08/043,339, Apr. 6, 1993, abandoned.

[51] Int. Cl.[6] .................................................... C07F 7/02
[52] U.S. Cl. .................. 504/193; 504/284; 504/289; 504/298; 549/4; 549/214; 548/406; 514/434; 514/419; 514/464; 514/613; 556/419
[58] Field of Search ..................... 549/214, 4; 556/419; 548/406; 504/289, 298, 284, 193; 514/434, 464, 613, 419

[56] References Cited

U.S. PATENT DOCUMENTS 4,804,653 2/1989 Strunk et al. .............................. 514/63

FOREIGN PATENT DOCUMENTS

| 0 360 417 A2 | 8/1989 | European Pat. Off. |
| 0 538 231 A1 | 10/1992 | European Pat. Off. |
| 63-284186 | 11/1988 | Japan |

OTHER PUBLICATIONS

J. Org., Chem 54(18) 4372–85, 1989.

Castells, Josep, et al., "Synthesis And Reactivity Of 2–(1, 3–Dithian–2–yl)indoles. IV.[1] Influence Of The N,N–Diethylcarbamoyl Indole Protecting Group," *Tetrahedron Letters*, vol. 47, No. 37, pp. 7911–7924 (1991).

(List continued on next page.)

*Primary Examiner*—Amelia Owens
*Attorney, Agent, or Firm*—Arnold, White & Durkee

[57] ABSTRACT

Plant disease caused by soil-borne fungus *Gaeumannonyces graminis* (Gg) is controlled by applying to the seed or the soil a fungicide which has the following general formula:

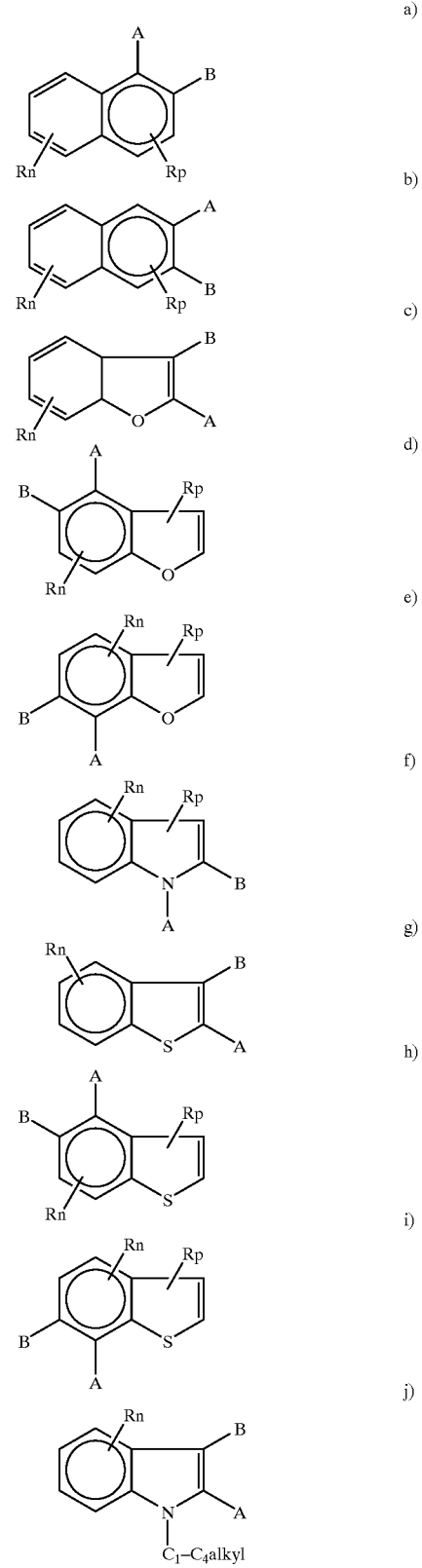

43 Claims, No Drawings

OTHER PUBLICATIONS

Gharpure, M., et al., "The N–tert–Butylcarbamoyl Directed Metalation Group For The Regiospecific Synthesis Of 2–Substituted Pyrroles And Indoles," *Synthesis*, pp. 1079–1082 (Dec. 1991).

Sengupta, Saumitra, et al., "Ni(0)–Catalyzed Cross Coupling Of Aryl O–Carbamates And Aryl Triflates With Grignard Reagents, Directed Ortho Metalation–Aligned Synthetic Methods For Polysubstituted Aromatics Via A 1,2–Dipole Equivalent," *J. Org. Chem.*, vol. 57, pp. 4066–4068 (1992).

Yagupol'skii, L. M., et al., "2–Trifluoromethylnaphthalene And Its Derivatives, II," *Zh. Obghch. Khim*, vol. 31, pp. 3696–3702 (1961).

Andrews, JF et al 'Pyrrole–2,3–quinodimethane analogs in the synthesis of indoles.' (1993) CA120: 191465.

FUNGICIDES FOR THE CONTROL OF TAKE-ALL DISEASE OF PLANTS

This application is a continuation of application Ser. No. 08/204,610, filed Mar. 8, 1994 which is now abandoned, is a continuation-in-part of U.S. patent application Ser. No. 08/043,339, filed Apr. 6, 1993, now abandoned.

FIELD OF THE INVENTION

This invention relates to a method for the control of Take-All disease in plants, particularly cereals, by the use of certain substituted aryl compounds, novel compounds for use in the method, and fungicidal compositions for carrying out the method.

BACKGROUND OF THE INVENTION

Take-all disease is a serious problem in the production of cereals, particularly wheat and barley. It is caused by the soil-borne fungus *Gaeumannomyces graminis* (Gg). The fungus infects the roots of the plant, and grows throughout the root tissue, causing a black rot. The growth of the fungus in the roots and lower stem prevents the plant from obtaining sufficient water and/or nutrients from the soil, and is manifested as poor plant vigor and, in severe instances of disease, by the formation of "whiteheads," which are barren or contain few, shriveled grains. Yield losses result. Gaeumannomyces species also infect other cereal crops, for example, rice and oats; and turf.

Currently the primary means of avoiding crop loss due to infestation of the soil by Gg has been to rotate the crop grown to one which is resistant to Gg. However, in areas where the primary crops are cereals, rotation is not a desirable practice, and an effective control agent is greatly desired.

A chemical means to control Gg and compounds useful for control of Gg are disclosed in co-pending U.S. Ser. No. 07/951,997, filed Oct. 2, 1992, (Phillion, et al.), hereby incorporated by reference.

It is an object of this invention to provide an effective method for control of Take-all disease in plants. It is a further object of this invention to provide compounds that control the growth of Gg in the soil so as to reduce crop loss. It is still a further object of this invention to provide fungicidal compositions that may be used for control of Take-all disease.

A process to prepare the compounds of this invention is analogous to the process disclosed in U.S. application Ser. No. 08/207,508 filed on Mar. 8, 1994 which issued as Pat. No. 5,482,974 on Jan. 9, 1996.

SUMMARY OF THE INVENTION

The present invention provides a method of controlling disease caused by Gaeumannomyces species in plants comprising applying to its seed or the soil, a fungicidally effective amount of a fungicide of the formula a) 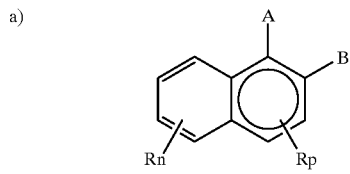

-continued b) 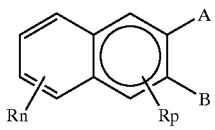

c) 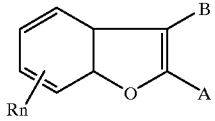

d) 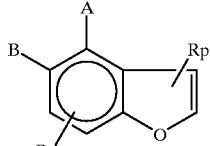

e) 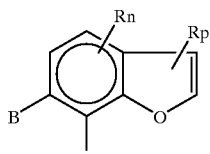

f) 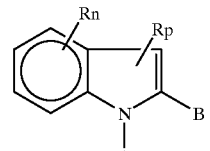

g) 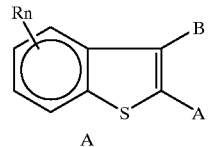

h) 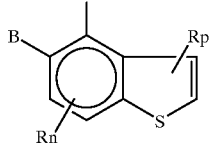

i) 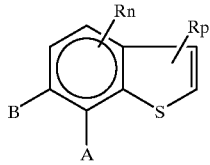

j) 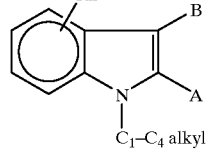

A is —C(X)-amine; B is —$W_m$—$Q(R_2)_3$; and A can be B when B is A except when the formula is f), then Q cannot be Si;
Q is C or Si;
W is —NH—, —O— or $NCH_3$—;
X is O or S;
m is 0 or 1, provided that m is 0 when Q is Si;
n is 0, 1, 2, or 3
p is 0, 1 or 2, and n plus p is equal to or less than 3; each R is independently selected from
  a) halo, formyl, cyano, amino, nitro, thiocyanato, isothiocyanato, trimethylsilyl, and hydroxy;

b) $C_1$–$C_4$ alkyl, alkenyl, alkynyl, $C_3$–$C_6$ cycloalkyl, and cycloalkenyl, each optionally substituted with halo, hydroxy, thio, amino, nitro, cyano, formyl, phenyl, $C_1$–$C_4$ alkoxy, alkylcarbonyl, alkylthio, alkylamino, dialkylamino, alkoxycarbonyl, (alkylthio)carbonyl, alkylaminocarbonyl, dialkylaminocarbonyl, alkylsulfinyl, or alkylsulfonyl;

c) phenyl, furyl, thienyl, pyrrolyl, each optionally substituted with halo, formyl, cyano, amino, nitro, $C_1$–$C_4$ alkyl, alkenyl, alkynyl, alkoxy, alkylthio, alkylamino, dialkylamino, haloalkyl, and haloalkenyl;

d) $C_1$–$C_4$ alkoxy, alkenoxy, alkynoxy, $C_3$–$C_6$ cycloalkyloxy, cycloalkenyloxy, alkylthio, alkylsulfinyl, alkylsulfonyl, alkylamino, dialkylamino, alkylcarbonylamino, aminocarbonyl, alkylaminocarbonyl, dialkylaminocarbonyl, alkylcarbonyl, alkylcarbonyloxy, alkoxycarbonyl, (alkylthio)carbonyl, phenylcarbonylamino, phenylamino, each optionally substituted with halo; each $R_2$ is independently selected from alkyl, alkenyl, alkynyl, cycloalkyl, cycloalkenyl and phenyl, each optionally substituted with $R_4$ or halogen; and wherein, when Q is C, $R_2$ may also be selected from halo, alkoxy, alkylthio, alkylamino, and dialkylamino; wherein two $R_2$ groups may be combined to form a cyclo group with Q; $R_4$ is $C_1$–$C_4$ alkyl, haloalkyl, alkoxy, alkylthio, alkylamino, or dialkylamino; or an agronomic salt thereof.

The term "amine" in —C(X)-amine means an unsubstituted, monosubstituted, or disubstituted amino radical, including nitrogen-bearing heterocycles. Examples of substituents for the amino radical include, but are not limited to, hydroxy; alkyl, alkenyl, and alkynyl, which may be straight or branched chain or cyclic; alkoxyalkyl; haloalkyl; hydroxyalkyl; alkylthio; alkylthioalkyl; alkylcarbonyl; alkoxycarbonyl; aminocarbonyl; alkylaminocarbonyl; cyanoalkyl; mono- or ialkylamino; phenyl, phenylalkyl or phenylalkenyl, each optionally substituted with one or more $C_1$–$C_6$ alkyl, alkoxy, haloalkyl, $C_3$–$C_6$ cycloalkyl, halo, or nitro roups; $C_1$–$C_4$ alkyl or alkenyl groups substituted with eterocycles, optionally substituted with one or more $C_1$–$C_4$ alkyl, alkoxy, haloalkyl, halo, or nitro groups. Examples of such nitrogen-bearing heterocycles, which are bonded at a nitrogen to —C(X)—, include, but are not limited to, morpholine, piperazine, piperidine, pyrrole, pyrrolidine, imidazole, and triazoles, each of which may be optionally substituted with one or more $C_1$–$C_6$ alkyl groups.

Specific examples of the amino radicals useful in the present invention include, but are not limited to, ethylamino, methylamino, propylamino, 2-methylethylamino, 1-propenylamino, 2-propenylamino, 2-methyl-2-propenylamino, 2-propynylamino, butylamino, 1,1-dimethyl-2-propynylamino, diethylamino, dimethylamino, N-(methyl)ethylamino, N-(methyl)-1,1-(dimethyl)ethylamino, dipropylamino, octylamino, N-(ethyl)-1-methylethylamino, 2-hydroxyethylamino, 1-methylpropylamino, chloromethylamino, 2-chloroethylamino, 2-bromoethylamino, 3-chloropropylamino, 2,2,2-trifluoroethylamino, cyanomethyl, methylthiomethylamino, (methylsulfonyl) oxyethylamino, 2-ethoxyethylamino, 2-methoxyethylamino, N-(ethyl)-2-ethoxyethylamino, 1-methoxy-2,2-dimethylpropylamino, cyclopropylamino, cyclobutylamino, cyclopentylamino, cyclohexylamino, methoxymethylamino, N-(methoxymethyl)ethylamino, N-(1-methylethyl)propylamino, 1-methylheptylamino, N-(ethyl)-1-methylheptylamino, 6,6-dimethyl-2-hepten-4-ynylamino, 1,1-dimethyl-2-propynylamino. Further examples include benzylamino, ethylbenzylamino, 3-methoxybenzylamino, 3-(trifluoromethyl)benzylamino, N-methyl-3-(trifluoromethyl)benzylamino, 3,4,5-trimethoxybenzylamino, 1,3-benzodioxol-5-ylmethylamino, phenylamino, 3-(1-methylethyl)phenylamino, ethoxyphenylamino, cyclopentylphenylamino, methoxyphenylamino, nitrophenylamino, 1-phenylethylamino, N-(methyl)-3-phenyl-2-propenylamino, benzotriazolylphenylmethyl, 2-pyridinylmethylamino, N-(ethyl)-2-pyridinylmethylamino, 2-thienylmethylamino, and furylmethylamino.

Further examples of amino radicals include methylhydrazino, dimethylhydrazino, N-ethylanilino, and 2-methylanilino. The amine may also be substituted with diethyl N-ethylphosphoramidic acid, t-butoxycarbonyl, methoxycarbonyl, ethoxycarbonyl, propoxycarbonyl, etc. Of these examples of the amino radical, ethylamino, propylamino, or allylamino is preferred.

Examples of B include, but are not limited to, trimethylsilyl, ethyldimethylsilyl, diethylmethylsilyl, triethylsilyl, dimethylpropylsilyl, dipropylmethylsilyl, dimethyl-1-(methyl)ethylsilyl, tripropylsilyl, butyldimethylsilyl, pentyldimethylsilyl, hexyldimethylsilyl, cyclopropyldimethylsilyl, cyclobutyldimethylsilyl, cyclopentyldimethylsilyl, cyclohexyldimethylsilyl, dimethylethenylsilyl, dimethylpropenylsilyl, chloromethyldimethylsilyl, 2-chloroethyldimethylsilyl, bromomethyldimethylsilyl, bicycloheptyldimethylsilyl, dimethylphenylsilyl, dimethyl-2-(methyl)phenylsilyl, dimethyl-2-fluorophenylsilyl, and other such silyl groups of the formula $Si(R_2)_3$. Of these examples of B, trimethylsilyl is preferred.

Further examples of B include 1,1-dimethylethyl, 1,1-dimethylpropyl, 1,1-dimethylbutyl, 1,1-dimethylpentyl, 1-ethyl-1-methylbutyl, 2,2-dimethylpropyl, 2,2-dimethylbutyl, 1-methyl-1-ethylpropyl, 1,1-diethylpropyl, 1,1,2-trimethylpropyl, 1,1,2-trimethylbutyl, 1,1,2,2-tetramethylpropyl, 1,1-dimethyl-2-propenyl, 1,1,2-trimethyl-2-propenyl, 1,1-dimethyl-2-butenyl, 1,1-dimethyl-2-propenyl, 1,1-dimethyl-2-propynyl, 1,1-dimethyl-2-butynyl, 1-cyclopropyl-1-methylethyl, 1-cyclobutyl-1-methylethyl, 1-cyclopentyl-1-methylethyl, 1-(1-cyclopentenyl)-1-methylethyl, 1-cyclohexyl-1-methylethyl, 1-(1-cyclohexenyl)-1-methylethyl, 1-methyl-1-phenylethyl, 1,1-dimethyl-2-chloroethyl, 1,1-dimethyl-3-chloropropyl, 1,1-dimethyl-2-methoxyethyl, 1,1-dimethyl-2-(methylamino) ethyl, 1,1-dimethyl-2-(dimethylamino)ethyl, 1,1-dimethyl-3-chloro-2-propenyl, 1-methyl-1-methoxyethyl, 1-methyl-1-(methylthio) ethyl, 1-methyl-1-(methylamino)ethyl, 1-methyl-1-(dimethylamino)ethyl, 1-chloro-1-methylethyl, 1-bromo-1-methylethyl, and 1-iodo-1-methylethyl. Of these examples of B, 1,1-dimethylpropyl, 1,1-diethylethyl or 1-methyl-1-cyclopentyl is preferred.

Further examples of B are 1,1-dimethylethylamino, 1,1-dimethylpropylamino, 1,1-dimethylbutylamino, 1,1-dimethylpentylamino, 1-ethyl-1-methylbutylamino, 2,2-dimethylpropylamino, 2,2-dimethylbutylamino, 1-methyl-1-ethylpropylamino, 1,1-diethylpropylamino, 1,1,2-trimethylpropylamino, 1,1,2-trimethylbutylamino, 1,1,2,2-tetramethylpropylamino, 1,1-dimethyl-2-propenylamino, 1,1,2-trimethyl-2-propenylamino, 1,1-dimethyl-2-butenylamino, 1,1-dimethyl-2-propynylamino, 1,1-dimethyl-2-butynylamino, 1-cyclopropyl-1-methylethylamino, 1-cyclobutyl-l-methylethylamino, 1-cyclopentyl-1-methylethylamino, 1-(l-cyclopentenyl)-1- methylethylamino, 1-cyclohexyl-1-methylethylamino, 1-(1-cyclohexenyl)-1-methylethylamino, 1-methyl-1-phenylethylamino, 1,1-dimethyl-2-chloroethylamino, 1,1-dimethyl-3-chloropropylamino, 1,1-dimethyl-2-methoxyethylamino, 1,1-dimethyl-2-(methylamino)-ethylamino, 1,1-dimethyl-2-(dimethylamino)ethylamino, and 1,1-dimethyl-3-chloro-2-propenylamino. Of these examples of B, 1,1-dimethylpropylamino, 1,1-ethylethylamino or 1-methyl-1-cyclopentylamino is preferred.

Further examples of B include 1,1-dimethylethoxy, 1,1-dimethylpropoxy, 1,1-dimethylbutoxy, 1,1-dimethylpentoxy, 1-ethyl-1-methylbutoxy, 2,2-dimethylpropoxy, 2,2-dimethylbutoxy, 1-methyl-1-ethylpropoxy, 1,1-diethylpropoxy, 1,1,2-trimethylpropoxy, 1,1,2-trimethylbutoxy, 1,1,2,2-tetramethylpropoxy, 1,1-dimethyl-2-propenoxy, 1,1,2-trimethyl-2-propenoxy, 1,1-dimethyl-2-butenoxy, 1,1-dimethyl-2-propynyloxy, 1,1-dimethyl-2-butynyloxy, 1-cyclopropyl-1-methylethoxy, 1-cyclobutyl-1-methylethoxy, 1-cyclopentyl-1-methylethoxy, 1-(1-cyclopentenyl)-1-methylethoxy, 1-cyclohexyl-1-methylethoxy, 1-(1-cyclohexenyl)-1-methylethoxy, 1-methyl-l-phenylethoxy, 1,1-dimethyl-2-chloroethoxy, 1,1-dimethyl-3-chloropropoxy, 1,1-dimethyl-2-methoxyethoxy, 1,1-dimethyl-2-(methylamino)ethoxy, 1,1-dimethyl-2-(dimethylamino)ethoxy, 1,1-dimethyl-3-chloro-2-propenoxy. Of these examples of B, 1,1-dimethylpropyloxy, 1,1-diethylethyloxy or cyclopentyloxy is preferred.

Further examples of B include 1-methylcyclopropyl, 1-methylcyclobutyl, 1-methylcyclopentyl, 1-methylcyclohexyl, 1-methylcyclopropylamino, 1-methylcyclobutylamino, 1-methylcyclopentylamino, and 1-methylcyclohexylamino.

$R_n$ may be any substituent(s) which do(es) not unduly reduce the effectiveness of the compounds to function in the method of disease control. $R_n$ is generally a small group; "n" is preferably 0 or 1. R is preferably methyl or halogen.

The invention also provides fungicidal compositions useful in said method.

As used herein, the term "alkyl", unless otherwise indicated, means an alkyl radical, straight or branched chain, having, unless otherwise indicated, from 1 to 10 carbon atoms. The terms "alkenyl" and "alkynyl" mean unsaturated radicals having from 2 to 7 carbon atoms. Examples of such alkenyl groups include ethenyl, 1-propenyl, 2-propenyl, 1-butenyl, 2-butenyl, 3-butenyl, 2-methyl-1-propenyl, 2-methyl-2-propenyl, 1-methyl-ethenyl, and the like. Examples of such alkynyl groups include ethynyl, 1-propynyl, 2-propynyl, 1,1-dimethyl-2-propynyl, and so forth. Substituent groups may also be both alkenyl and alkynyl, for example, 6,6-dimethyl-2-hepten-4-ynyl.

As used herein, the term "alkoxy" means an alkyl group having, unless otherwise indicated, from 1 to 10 carbon atoms connected via an ether linkage. Examples of such alkoxy groups include methoxy, ethoxy, propoxy, 1-methylethoxy, and so forth.

As used herein, the term "alkoxyalkyl" means an ether radical having, unless otherwise indicated, from 1 to 10 carbon atoms. Examples of such alkoxyalkyl groups include methoxymethyl, methoxyethyl, ethoxymethyl, ethoxyethyl, and so forth.

As used herein, the terms "monoalkylamino" and "dialkylamino" each mean an amino group having, respectively, 1 or 2 hydrogens replaced with an alkyl group.

As used herein, the term "haloalkyl" means an alkyl radical having one or more hydrogen atoms replaced by halogens, including radicals having all hydrogen atoms substituted by halogen. Examples of such haloalkyl groups are fluoromethyl, difluoromethyl, trifluoromethyl, chloromethyl, trichloromethyl, and so forth.

As used herein, the term "halo" means a radical selected from chloro, bromo, fluoro, and iodo.

DETAILED DESCRIPTION OF THE INVENTION

Control of Gg diseases, including Take-All, using a chemical control agent may be accomplished in several ways. The agent may be applied directly to soil infested with Gg, for example, at the time of planting along with the seed. Alternatively, it may applied to the soil after planting or germination. Preferably, however, it is applied to the seed in a coating prior to planting. This technique is commonly used in many crops to provide fungicides for control of various phytopathological fungi.

Compositions of the present invention are comprised of a fungicidally effective amount of one or more of the compounds described above and one or more adjuvants. The active ingredient may be present in such compositions at levels from 0.01 to 95 percent by weight. Other fungicides may also be included to provide a broader spectrum of fungal control. The choice of fungicides will depend on the crop and the diseases known to be a threat to that crop in the location of interest.

The fungicidal compositions of this invention, including concentrates which require dilution prior to application, may contain at least one active ingredient and an adjuvant in liquid or solid form. The compositions are prepared by admixing the active ingredient with an adjuvant including diluents, extenders, carriers, and conditioning agents to provide compositions in the form of finely-divided particulate solids, granules, pellets, solutions, dispersions or emulsions. Thus, it is believed that the active ingredient could be used with an adjuvant such as a finely-divided solid, a liquid of organic origin, water, a wetting agent, a dispersing agent, an emulsifying agent or any suitable combination of these.

Suitable wetting agents are believed to include alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters, petroleum sulfonates, sulfonated vegetable oils, ditertiary acetylenic glycols, polyoxyethylene derivatives of alkylphenols (particularly isooctylphenol and nonylphenol) and polyoxyethylene derivatives of the mono-higher fatty acid esters of hexitol anhydrides (e.g., sorbitan). Preferred dispersants are methyl, cellulose, polyvinyl alcohol, sodium lignin sulfonates, polymeric alkyl naphthalene sulfonates, sodium naphthalene sulfonate, and polymethylene bisnaphthalene sulfonate. Stabilizers may also be used to produce stable emulsions, such as magnesium aluminum silicate and xanthan gum.

Other formulations include dust concentrates comprising from 0.1 to 60% by weight of the active ingredient on a suitable extender, optionally including other adjuvants to improve handling properties, e.g., graphite. These dusts may be diluted for application at concentrations within the range of from about 0.1–10% by weight.

Concentrates may also be aqueous emulsions, prepared by stirring a nonaqueous solution of a water-insoluble active ingredient and an emulsification agent with water until uniform and then homogenizing to give stable emulsion of very finely-divided particles. Or they may be aqueous suspensions, prepared by milling a mixture of a water-insoluble active ingredient and wetting agents to give a suspension, characterized by its extremely small particle size, so that when diluted, coverage is very uniform. Suitable concentrations of these formulations contain from about 0.1–60% preferably 5–50% by weight of active ingredient.

Concentrates may be solutions of active ingredient in suitable solvents together with a surface active agent. Suitable solvents for the active ingredients of this invention for use in seed treatment include propylene glycol, furfuryl alcohol, other alcohols or glycols, and other solvents which do not substantially interfere with seed germination. If the active ingredient is to be applied to the soil, then solvents such as N,N-dimethylformamide, dimethylsulfoxide, N-methylpyrrolidone, hydrocarbons, and water-immiscible ethers, esters, or ketones.

The concentrate compositions herein generally contain from about 1.0 to 95 parts (preferably 5–60 parts) active ingredient, about 0.25 to 50 parts (preferably 1–25 parts) surface active agent and where required about 4 to 94 parts solvent, all parts being by weight based on the total weight of the concentrate.

For application to the soil at the time of planting, a granular formulation may be used. Granules are physically stable particulate compositions comprising at least one active ingredient adhered to or distributed through a basic matrix of an inert, finely-divided particulate extender. In order to aid leaching of the active ingredient from the particulate, a surface active agent such as those listed hereinbefore, or for example, propylene glycol, can be present in the composition. Natural clays, pyrophyllites, illite, and vermiculite are examples of operable classes of particulate mineral extenders. The preferred extenders are the porous, absorptive, preformed particles such as pre-formed and screened particulate attapulgite or heat expanded, particulate vermiculite and the finely-divided clays such as kaolin clays, hydrated attapulgite or bentonitic clays. These extenders are sprayed or blended with the active ingredient to form the fungicidal granules.

The granular compositions of this invention may contain from about 0.1 to about 30 parts by weight of active ingredient per 100 parts by weight of clay and 0 to about 5 parts by weight of surface active agent per 100 parts by weight of particulate clay.

The method of the present invention may be carried out by mixing the composition comprising the active ingredient into the seed prior to planting at rates from 0.01 to 50 g per kg of seed, preferably from 0.1 to 5 g per kg, and more preferably from 0.2 to 2 g per kg. If application to the soil is desired, the compounds may be applied at rates from 10 to 1000 g per hectare, preferably from 50 to 500 g per hectare. The higher application rates will be needed for situations of light soils or greater rainfall or both.

The compounds useful in the present invention may be prepared by methods known to those of ordinary skill in the art. The following examples illustrate some of these methods and are illustrative only; they are not meant to be limiting in any way.

Unless otherwise indicated, percentages are given as weight/weight. Melting points and boiling points are reported uncorrected. Thin layer chromatography was carried out with varying concentrations of ethyl acetate -hexanes elutions. Tetrahydrofuran and ether solvents were distilled from sodium metal/benzophenone immediately prior to use. N,N,N', N'-(Tetramethyl)-ethylenediamine was distilled from calcium hydride prior to use. All other reagents were purchased from Aldrich or Lancaster and used without purification. A measured physical property is reported for each example or the elemental analysis is given at the end of the examples.

The following abbreviations have the meanings shown:

| | |
|---|---|
| n-BuLi | n-Butyl lithium |
| s-BuLi | sec-Butyl lithium |
| DMF | Dimethylformamide |
| TMSC1 | Trimethylsilyl chloride |
| THF | Tetrahydrofuran |
| TMEDA | N,N,N',N'-(tetramethyl)ethylenediamine |
| eq | equivalent(s) |
| aq | aqueous |
| sat | saturated |
| min | minutes |
| h | hours |
| MeI | Methyl iodide |
| TLC | Thin Layer Chromatography |
| HPLC | High Pressure Liquid Chromatography |
| RC | Radial Chromatography |
| GLC | Gas-liquid Chromatography |
| RT | room temperature |
| m.p. | melting point |

GENERAL METHODS

The phrase "worked up in the usual manner" refers to treatment of the reaction mixture with 10% aq citric acid, extraction with diethyl ether, washing of the combined organic extracts with sat brine solution, drying of the organic extract over $MgSO_4$, and evaporation to dryness in vacuo to afford the crude product. The phrase "appropriate" means a compound having the substituents desired for the final product of the reaction.

Method A. Ortho-introduction of Electrophiles into N,N-dialkylbenzamides.

1.3M s-BuLi in cyclohexane (1.1 to 1.2 molar eq) was added dropwise to a dry-ice/acetone or an ether/liquid nitrogen cooled 1.0M solution of TMEDA (1.0 to 1.2 molar eq) in THF, followed by the dropwise addition of the appropriate N,N-dialkylbenzamide (1.0 eq) in THF. The resulting reaction mixture was stirred for 30–60 min at −78° C. to ensure complete aryl anion formation, then was cooled to $\leq 90°$ C. with an ether/liquid nitrogen bath and quenched by the careful addition of the appropriate electrophile. The reaction was allowed to warm slowly to 0° C. then was worked up in the usual manner. If needed, the crude product was purified by chromatography, recrystallization or distillation.

Method B. Ortho-introduction of Electrophiles into N,N-dialkylbenzamides via Inverse Addition.

1.3M s-BuLi in cyclohexane (1.2 eq) was added dropwise to an ether/liquid nitrogen cooled 1.0M solution of TMEDA (1.2 eq) in THF, followed by the drop-wise addition of the appropriate N,N-dialkylbenzamide (1.0 eq) in THF. The internal reaction temperature was maintained between −80 and −95° C. during both additions. After addition, the cooling bath was replaced with dryice/acetone, and the resulting reaction was stirred at −78° C. for 1 h. This solution was then cannulaed into a solution of an excess of the appropriate electrophile in THF at a rate which maintained the internal reaction temperature below −80° C. with an ether/liquid nitrogen bath. The resulting reaction mixture was slowly allowed to 0° C. then purified in the manner described below for each compound.

Method C. Ortho-introduction of Electrophiles into N-alkylbenzamides.

1.3M s-BuLi in cyclohexane (2.1 to 2.2 eq) was added dropwise to a dry-ice/acetone or an ether/liquid nitrogen cooled 1.0M solution of TMEDA (1.0 to 1.2 eq) in THF, followed by the dropwise addition of the appropriate N-alkylbenzamide (1.0 eq) in THF. The resulting reaction mixture was stirred for 30–60 min at −78° C. to ensure complete aryl anion formation, then was cooled to $\leq$−90° C. with an ether/liquid nitrogen bath and quenched by the careful addition of the appropriate electrophile. The reaction was allowed to warm slowly to −30° C. then was worked up in the usual manner. If needed, the crude product was purified by chromatography, recrystallization or distillation.

Method D. A tert-alkylamine (3 parts) was added to 1.6M n-butyl lithium in hexanes (2.5 parts) in THF, maintaining the internal reaction temperature $\leq$−70° C. The resulting solution was briefly warmed to 0° C., then was recooled to $\leq$−70° C. A solution of either of the products from examples h or i (1 part) dissolved in THF was added to this cold solution of the N-lithio tert-alkylamine, keeping the internal reaction temperature $\leq$−50° C. This was warmed to 0° C. and stirred for 1 hour, then was partitioned between ether and aqueous sodium bicarbonate. The ether phase was washed with water, filtered to remove solids, dried (MgSO$_4$), concentrated, and purified by chromatography to afford the 1-(2-oxazolinyl)-2-(tert-alkylamino)naphthalene as an oil.

Method E. The product of Method D was stirred with an excess of 30% hydrogen bromide in acetic acid to convert the oxazoline ring to its 2-bromoalkylamide. After 30 minutes, the reaction mixture was poured over ice then partitioned between methylene chloride and excess aqueous potassium carbonate. The methylene chloride was dried (MgSO$_4$) and concentrated to give a high yield of the N-(2-bromoalkyl) 2-(tert-alkylamino)-1-naphthamide as a solid.

Method F. Tributyltin hydride (1.6 parts) and catalytic 2,2'-azobis(2-methyl propionitrile) were added to an 0.7–0.9M slurry of the product of Method E (1 part) in benzene. This was heated in a sealed vessel for 13–20 hours at 75° C., then was partitioned between ether and aqueous sodium bicarbonate. The ether phase was dried (MgSO$_4$), concentrated and recrystallized from hexanes to afford a low yield of the N-alkyl 2-(tert-alkylamino)-1-naphthamide as a solid.

Method G. In a Parr apparatus, a solution of the product of Method E (1 part) and triethylamine (2.2 parts) in ethanol was hydrogenated (50 psi) over catalytic 5% palladium on carbon for 2 hours. The resulting mixture was filtered through celite, concentrated, and the residue partitioned between methylene chloride and water. The methylene chloride phase was washed with brine, dried (MgSO$_4$), and purified by chromatography to afford moderate yields of the N-ethyl 2-(tert-alkylamino)-1-naphthamide as a solid.

Method H. Potassium tert-butoxide (5 parts) was added to an 0.3M solution of the product of Method D (1 part) in anhydrous DMSO and heated in a sealed vessel at 110–120° C. for 0.5–1.0 hour, then the resulting reaction mixture was partitioned between ether and water. The ether phase was washed with water, dried (MgSO$_4$) and concentrated to afford crude N-(1-propenyl) 2-(tert-alkylamino)-1-naphthamide. In a Parr apparatus, a solution of this alkenylamide in methanol was hydrogenated (50–60 psi) over catalytic PtO$_2$ for 3.5–6.0 hours. The resulting mixture was filtered through celite, concentrated, and purified by chromatography to afford moderate yields of the N-propyl 2-(tert-alkylamino)-1-naphthamide as a solid.

Method I. A 35% oil dispersion of potassium hydride (1 part) was added to a solution of a tert-alkanol in dry 1,2-dimethoxyethane. This mixture was briefly refluxed to achieve complete formation of the potassium alkoxide, then was cooled to room temperature and the product of example j (0.9 part) was added. The resulting mixture was briefly refluxed to achieve substitution of the chloride with the alkoxide, then was cooled and partitioned between ether and water. The organic layer was washed with brine, dried (MgSO$_4$), decolorized with activated carbon, then was filtered through silica gel and concentrated. The residue was passed through a 4 inch plug of silica gel by eluting first with hexanes to remove the mineral oil then with 1:4 ethyl acetate/hexanes to give the desired naphthonitrile. This purified 2-tert-alkoxy-1-naphthonitrile was dissolved in tert-amyl alcohol and enough potassium hydroxide pellets were added to maintain saturation during reflux. The mixture was refluxed for 5 hours, then was concentrated under vacuum and the residue was partitioned between ether and water. The organic layer was washed with brine, dried (MgSO$_4$) and filtered through silica gel. Then the filtrate was concentrated and the residue triturated with hexanes to give the 2-tert-alkoxy-1-naphthamide as a solid.

Method J. To a solution of the primary naphthamide from Method I (1 part) in dry THF was added solid lithium bis(trimethylsilyl)amide (1.1 part). After stirring this mixture for 5 min, the appropriate alkyl halide (2–5 parts) was added and the reaction was refluxed for 3 hours. This was partitioned between ether and water, and the organic layer was washed with brine, dried (MgSO$_4$), filtered through silica gel, and concentrated to give the crude N-alkyl 2-tert-alkoxy-1-naphthamide which was purified by recrystallization or chromatography.

Method K. To a solution of the primary naphthamide from Method I (1 part) and tetrabutylammonium hydrogen sulfate (0.02 part) in toluene was added an equal volume of 50% NaOH and the appropriate alkyl halide (2.2 parts), and the mixture was refluxed for 45 min. This was partitioned between ether and water, and the organic layer was washed with brine, dried (MgSO$_4$), filtered through silica gel, and concentrated to give the crude N-alkyl 2-tert-alkoxy-1-naphthamide which was purified by recrystallization or chromatography.

Method L. 2- or 3-Vinyl thiophene or 2- or 3-vinylfuran (2.0–3.2 parts) was added to an 0.9–1.8M solution of 3-trimethylsilyl propiolyl chloride (1 part) in methylene chloride, and the mixture was heated in a sealed vessel at 60–80° C. for 11–64 hours. This was cooled and added to an ice-water cooled, stirred mixture of aqueous 70% ethylamine (5–10 parts) in methylene chloride and water. The resulting reaction mixture was stirred at room temperature for 30 minutes, then the organic layer was separated and washed with dilute aqueous HCl, followed with aqueous sodium bicarbonate and then brine. The organic phase was dried (MgSO$_4$) and purified by chromatography. This dihydrobenzofuran or dihydrobenzothiophene (1 part) was aromatized with DDQ (1 part) by refluxing in toluene for 30 minutes. The resulting solution was filtered, concentrated, and purified by chromatography to afford the desired benzofuran or benzothiophene as a solid.

STARTING MATERIALS

Example a. 2- and 3-benzothiophenecarboxylic acids.

To a suspension of aluminum chloride (13.4 g, 0.1 mol) in 100 mL methylene chloride at −60° C. under a nitrogen atmosphere was added a solution of trichloroacetyl chloride (11 mL, 0.1 mol) in 50 mL methylene chloride at between −50 and −60° C. After the completion of addition, the mixture was warmed to between −30 and −40° C. and stirred for an additional 45 min at that temperature range. After that, a solution of benzothiophene (13.4 g, 0.1 mol) in 50 mL methylene chloride was added slowly at between −30 and −40° C. The resulting reaction mixture was warmed to 0° C. and stirred for 2 h. The mixture was poured into 50 mL of 2N HCl and extracted with ether. The ether solution was washed with water, sat sodium bicarbonate, and brine; dried; and concentrated in vacuo. The crude product was dissolved in 100 mL THF and treated with 20% KOH solution until basic. Ether was added and the two layers separated. The aq layer was washed with additional ether and then acidified with conc HCl. The solid which formed was filtered and air-dried to give 6 g of a mixture of acids. 3-Benzothiophenecarboxylic acid was the major component.

Example b. N-Ethyl-3-benzothiophenecarboxamide.

A mixture of the acids of example a (3.6 g, 20 mmol) in 16 mL thionyl chloride containing a few drops of DMF was refluxed for 3 h, then was cooled, and excess thionyl chloride was removed under reduced pressure to give a mixture of acid chlorides. A solution of this mixture of acid chlorides in methylene chloride was added dropwise to 20 mL of 70% aq ethylamine at −20 ° C., then was warmed to RT and stirred for 2 h. Water was added and the two layers were separated. The organic layer was washed with brine, dried and concentrated in vacuo. The residue was purified by flash chromatography with 30% ethyl acetate-hexane to give 3.1 g of product.

Example c. 2-Benzothiophenecarboxylic acid.

To a solution of benzothiophene (20 g, 0.15 mol) in 120 mL THF at −30° C. was added dropwise 2.5M of n-BuLi in hexane (70 mL, 0.175 mol) at between −20 and −30 ° C. The solution was warmed to 0° C., stirred for 3 h and poured into dry ice. Water and ether were added. The aq layer was separated and acidified with conc HCl. The solid which formed was filtered and air-dried overnight to give the crude acid.

Example d. N-Ethyl-2-benzothiophenecarboxamide.

The acid of example c (5.4 g) in 20 mL thionyl chloride containing 6 drops of DMF was refluxed for 2 h, then cooled and excess thionyl chloride was removed under reduced pressure. The crude acid chloride was dissolved in methylene chloride and added slowly to 20 mL methylene chloride and 30 mL of 70% ethylamine at −20° C. After 2 h at ambient temperature, the mixture was poured into water and extracted with methylene chloride. The organic layer was washed with brine, dried and concentrated in vacuo. The residue was chromatographed on silica gel with 35% ethyl acetate-hexane as eluent to give 1.9 g of analytically pure product.

Example e. 2- and 3-Trichloroacetylbenzothiophenes.

Six-fold quantities of the reagents used in the method for example a, with the omission of the sodium hydroxide hydrolysis step, yielded 130 g of a mixture of 2- and 3-trichloroacetylbenzothiophenes of which the 3-isomer was the major component.

Example f. N-Allyl-3-benzothiophenecarboxamide.

To a solution of the mixture of example e (9 g) in 40 mL methylene chloride at 10° C. was added dropwise allylamine (4 g), and the resulting reaction solution was stirred at RT for 18 h. The solution was washed with 2N HCl and brine, dried and concentrated. Flash chromatography of the residue with 20% ethyl acetate-hexane gave 2.7 g of the desired product.

Example g. 2-Methoxy-1-naphthoic acid

Potassium carbonate (111 g, 803 mmol) was added to a mixture of 2-hydroxy-l-naphthoic acid (50.0 g, 266 mmol) and methyl iodide (189 g, 1330 mmol) in DMF (500 mL). The resulting mixture was heated at 80° C. overnight, then was partitioned between ether and water. The organic was washed with dilute aqueous HCl, dried ($MgSO_4$), and concentrated to afford methyl 2-methoxynaphthoate as an oil.

50% Aqueous sodium hydroxide was added to a solution of this methyl 2-methoxynaphthoate in methanol (400 mL). The mixture was refluxed, and water (300 mL) was added at a rate which kept the forming sodium 2-methoxynaphthoate in solution. After the water was added, the reaction was refluxed an additional 3 hours, then allowed to stand at room temperature overnight. The resulting solid mass was acidified with concentrated HCl, then was diluted with water (1 liter) and the product collected by filtration. Vacuum drying gave 50.96 g of 2-methoxy-1-naphthoic acid, a 95% yield.

Example h. 2-(2-methoxy-1-naphthyl) oxazoline

Oxalyl chloride (6.3 g, 49.6 mmol) was added to a slurry of the product of example g (5.0 g, 24.8 mmol) and DMF (2 drops as catalyst) in methylene chloride (25 mL). After about 30 minutes the reaction formed a solution which was then briefly refluxed until gas evolution ceased. This was concentrated under vacuum to remove the excess oxalyl chloride. The solid acid chloride was dissolved in methylene chloride (10 mL) and added dropwise to an ice-water cooled and mechanically stirred mixture of 2-bromoethylamine hydrobromide (10.15 g, 49.5 mmol) and potassium carbonate (6.84 g, 49.5 mmol) in water (50 mL) and methylene chloride (40 mL). The resulting mixture was stirred at room temperature for 15 minutes, then was partitioned between methylene chloride and water. The organic was washed with aqueous HCl followed with aqueous sodium bicarbonate, then was dried ($MgSO_4$) and concentrated to afford 5.5 g of solid N-(2-bromoethyl) 2-methoxy-1-naphthamide, a 72% yield.

50% Aqueous sodium hydroxide (30 mL) was added to a solution of N-(2-bromoethyl) 2-methoxy-1-naphthamide (13 g, 42.2 mmol) and benzyltriethylammonium chloride (1.2 g, 5.3 mmol) in methylene chloride (120 mL). The resulting mixture was vigorously stirred at room temperature for 2 hours, then was diluted with water and the layers separated. The organic phase was washed with brine, dried ($MgSO_4$), and concentrated to give 9.5 g of solid 2-(2-methoxy-1-naphthyl)oxazoline, a 99% yield.

Example i. 2-(2-methoxy-1-naphthyl)-5-methyloxazoline

Oxalyl chloride (6.3 g, 49.6 mmol) was added to a slurry of the product of example g (5.0 g, 24.8 mmol) and DMF (2 drops as catalyst) in methylene chloride (25 mL). After about 30 minutes the reaction formed a solution which was then briefly refluxed until gas evolution ceased. This was concentrated under vacuum to remove the excess oxalyl chloride. The solid acid chloride was dissolved in methylene chloride (10 mL) and added dropwise to an ice-water cooled mixture of 2-hydroxy propylamine (9.3 g, 124 mmol) in methylene chloride (40 mL). The resulting reaction mixture was warmed to room temperature and washed with aqueous HCl, followed with aqueous sodium bicarbonate. The organic phase was dried ($MgSO_4$) and concentrated to an oil which was crystallized from ethyl acetate to give 4.00 g of solid N-(2-hydroxy-1-propyl) 2-methoxy-1-naphthamide, a 62% yield.

This N-(2-hydroxy-1-propyl) 2-methoxy-1-naphthamide (4.00 g, 15.4 mmol) was added in portions to ice-water cooled thionyl chloride (7.4 g, 62 mmol). This was then stirred at room temperature and after 1 hour the slurry which had formed was diluted with ether and collected by filtration, then was partitioned between ether and aqueous sodium hydroxide. This ether solution was dried ($MgSO_4$) and concentrated to afford 2-(2-methoxy-1-naphthyl)-5-methyloxazoline as an oil.

Example j. 2-chloro-1-naphthonitrile

Ethyl cyanoacetate (111.0 g, 982 mmol) was added to a suspension of potassium hydroxide pellets (52.0 g, 789 mmol) and potassium cyanide (16.0 g, 246 mmol) in dry DMF (500 mL). This was stirred at ambient temperature for 30 minutes, then 85% 2-nitro naphthalene (40.0 g, 197 mmol) was added to the reaction mixture. After stirring at room temperature for 22 hours, the reaction was refluxed for 10 minutes, then 10% NaOH (300 mL) was added and refluxing was continued for an additional 2 hours. The resulting mixture was cooled and poured onto crushed ice and extracted with chloroform. The organic phase was washed with water followed with brine, then was dried (MgSo4), decolorized with activated carbon, and filtered through silica gel. The filtrate was concentrated and triturated first with ether and then with 1:1 ethyl acetate/hexane to give 23.0 g of 2-amino 1-naphthonitrile as a yellow solid. tert-Butyl nitrite (23.5 g, 205 mmol) was added dropwise to an ice-water cooled mixture of cupric chloride (20.3 g, 151 mmol) in a solution 2-amino-1-naphthonitrile (23.0 g, 137 mmol) in dry acetonitrile (250 mL). Gas evolution was controlled by the rate of addition of the tert-butyl nitrite. The resulting reaction mixture was stirred at 0° C. for 30 minutes, then at room temperature for 30 minutes. This was poured into cold, dilute aqueous HCl and the precipitate which formed was filtered, vacuum dried, and kugelrohr distilled (180° C., 3.5 torr) to give 15.5 g of white, crystalline 2-chloro-1-naphthonitrile, a 60% yield.

EXAMPLE 1

N-Ethyl-4-fluoro-2-(trimethylsilyl)-1-naphthalenecarboxamide.

A 1.3 M solution of s-BuLi in cyclohexane (40.7 mL, 52.9 mmol) was added to a liquid nitrogen-cooled solution of TMEDA (8.68 mL, 57.5 mmol) in THF (50 mL), maintaining the reaction temperature at -90° C. throughout the addition. The resulting solution was stirred 5 min, a solution of N-ethyl-4-fluoro-1-naphthalene-carboxamide (5.00 g, 23.0 mmol) in THF (15 mL) was added, and the resulting purple solution was stirred for 10 min at -90° C. TMSCl (8.76 mL, 69.0 mmol) was added, and after 10 min the cold bath was removed. The mixture slowly warmed to RT. The mixture was quenched with 100 mL 25% citric acid and extracted with ether (3×200 mL). The combined extracts were dried (MgSO$_4$) and concentrated to a yellow powder which was purified by chromatography with ethyl acetate/hexanes to give 1.36 g of the desired amide, a 20% yield. m.p. 134–136° C.

EXAMPLE 2

N,N-Diethyl-2-[(iodomethyl)dimethylsilyl]-1-naphthalenecarboxamide.

A solution of 1.3M s-BuLi in cyclohexane (20.3 mL, 26.4 mmol) was added dropwise to an ether/liquid nitrogen-cooled solution of TMEDA (4.0 mL, 26.5 mmol) in THF (15 mL), maintaining the internal reaction temperature <-80° C. To this mixture was added a solution of N,N-diethyl-1-naphthalenecarboxamide (5.0 g, 22.0 mmol) in THF (10 mL), again maintaining the internal reaction temperature <-80° C. The resulting solution was stirred with dry ice/acetone cooling for 30 min, then was recooled to <-80° C. with an ether/liquid nitrogen bath while chloromethyl dimethylsilyl chloride (3.8 mL, 28.8 mmol) was added dropwise. The mixture was warmed to RT to afford a green solution which was diluted with ether and extracted with dilute aq citric acid (2 X), followed with sat aq NaHCO$_3$. The ether solution was dried (MgSO$_4$), concentrated, and chromatographed with 3:17 ethyl acetate/hexanes to afford 4.3 g of N,N-diethyl-2-[(chloromethyl)dimethylsilyl]-1-naphthalenecarboxamide as a yellow oil, a 59% yield.

A solution of this naphthalenecarboxamide (1.0 g, 3.0 mmol) and NaI (13.5 g, 90 mmol) in acetonitrile (90 mL) was refluxed overnight, then was diluted with ether and filtered through celite to remove most of the salts. The filtrate was then concentrated and eluted through a plug of silica gel with ethyl acetate. Concentration of the ethyl acetate afforded 1.25 g of the desired compound as a yellow oil, a 98% yield.

EXAMPLE 3

N,N-Diethyl-2-(trimethylsilyl)-1-naphthalenecarboxamide.

N,N-Diethyl-1-naphthalenecarboxamide was reacted with 2 eq TMSCl according to General Method A. The resulting reaction mixture was worked up in the usual manner, then purified by chromatography with 20% ethyl acetate/80% hexanes to afford 2.1 g of the desired compound as a clear oil, a 71% yield.

EXAMPLE 4

N-Ethyl-2-(trimethylsilyl)-1-naphthalenecarboxamide.

N-Ethyl-1-naphthalenecarboxamide was reacted with 2 eq TMSCl according to General Method C. The resulting reaction mixture was worked up in the usual manner, then purified by recrystallization from cold ethyl acetate/hexanes to afford 1.6 g of desired compound as a white solid, a 58% yield. m.p. 141–143° C.

EXAMPLE 5

N-Ethyl-3-(trimethylsilyl)-2-naphthalenecarboxamide.

N-Ethyl-2-naphthalenecarboxamide was reacted with 2 eq TMSCl according to General Method C. The resulting reaction mixture was worked up in the usual manner, then purified by chromatography with 3:7 ethyl acetate/hexanes to afford 3.3 g of the desired compound as a white solid, a 17% yield. m.p. 132–136° C.

EXAMPLE 6

2-(1,1-Dimethylethoxy)-N-ethyl-1-naphthalenecarboxamide.

A solution of 1.3M s-BuLi in cyclohexane (34 mL, 44 mmol) was added dropwise to a -78° C. cooled solution of N-ethyl-1-naphthalenecarboxamide (20 mmol) and TMEDA (6.0 mL, 40 mmol) in THF (100 mL). After 30 min, MgBr$_2$.Et$_2$O (15.5 g, 60 mmol) was added portion wise, and the reaction was briefly warmed to ambient temperature then was recooled to -78° C. After 1 h at -78° C., t-butylperoxy benzoate (4.3 g, 22 mmol) was added. The resulting reaction was warmed to -30° C. and worked up in the usual manner, then was purified by chromatography with 3:7 ethyl acetate/hexanes to afford 1.7 g of desired compound as a white solid, a 33% yield. m.p. 126–127° C.

EXAMPLE 7

N-Ethyl-2-(trimethylsilyl)-lH-indole-1-carboxamide.

NaH (0.9 g, 37.5 mmol) was added in portions to a 0° C. cooled solution of indole (2.93 g, 25 mmol) in THF (100 mL). After 30 min, ethyl isocyanate (1.78 g, 25 mmol) was added dropwise. The reaction mixture was stirred at RT overnight, then was quenched with 25% citric acid in water (50 mL) and extracted with ethyl acetate (3 X). These organic extracts were combined, dried (MgSo$_4$), and recrystallized from ether/hexanes to afford 1.3 g of N-(ethylaminocarbonyl)indole as a tan solid, a 28% yield. m.p. 71–73° C.

A solution of 1.3M s-BuLi in cyclohexane (8.97 mL, 11.66 mmol) was added dropwise to a -78° C. cooled solution of N-(ethylaminocarbonyl)indole (1.0 g, 5.3 mmol) and 2,2,6,6-tetramethylpiperidine (0.75 g, 5.3 mmol) in THF (50 mL). After 30 min, TMSCl (0.9 g, 8 mmol) was added in a single portion, then the cold bath was removed to allow the reaction to warm over 1 h. This mixture was quenched with 25% citric acid in water (50 mL) and extracted with ethyl acetate (3 X). The organic extracts were combined, dried ($MgSO_4$), concentrated, and recrystallized from ether/hexanes to afford 1.1 g of desired compound as a white solid, an 80% yield. m.p. 96–99° C.

EXAMPLE 8
N-Ethyl-2-(trimethylsilyl)-benzo[b]thiophene-3-carboxamide.

A solution of the compound of example b (2 g, 10 mmol) in THF was treated with 2.5M of n-BuLi in hexane and quenched with TMSCl under the conditions used in Example 9 to give 2.3 g of the desired product as white solid, an 82.7% yield. m.p. 121–124° C.

EXAMPLE 9
N-Ethyl-3-(trimethylsilyl)benzo[b]thiophene-2-carboxamide.

To a solution of the amide of example d (1.5 g, 7.5 mmol) in 40 mL THF at –78° C. under a positive $N_2$ atmosphere was added dropwise 2.5M of n-BuLi in hexane (7.5 mL, 18 mmol) and stirring was continued for additional 0.5 h. Then TMSCl (5 mL) was added slowly at below –70° C. After 0.5 h at below –70° C., the solution was warmed to 0° C. and quenched with ice water. Methylene chloride was added. The aq layer was separated and extracted with additional methylene chloride. The combined organic layers were washed with brine, dried and concentrated in vacuo. The residue was chromatographed on silica gel with 20% ethyl acetate-hexane to give 1.8 g of the product as a white solid, a yield of 85.7%. m.p. 131–134° C.

EXAMPLE 10
N-Ethyl-1-Methyl-2-(trimethylsilyl)-1H-indole-3-carboxamide.

To a solution of indole (6.5 g, 60 mmol) in 25 mL THF at 10° C. was added trifluoroacetic anhydride (12 mL, 80 mmol) and the resulting reaction mixture was stirred at 10–20° C. for 30 min. The mixture was then poured into water, and the precipitate was filtered and air-dried to give 11.5 g of 3-trifluoroacetyl-1H-indole.

To a solution of this compound (11 g, 50 mmol) in 100 mL acetone were added MeI (10 mL, 150 mmol) and potassium carbonate (18 g), and stirring was continued at RT for 2 h. Acetone was removed in vacuo. Water and methylene chloride were added to the residue. The organic layer was separated, washed with brine, dried and concentrated in vacuo to yield crude 1-methyl-3-trifluoroacetyl-1H-indole. To this was added 12 g NaOH in 80 mL water, and the mixture was refluxed for 1.5 h. The solution was cooled and acidified with conc HCl. The solid was filtered and air-dried to give 7.5 g of 1-methyl-1H-indole-3-carboxylic acid.

The title compound was obtained as a white solid in an overall yield of 56.8% from 1-methyl-1H-indole-3-carboxylic acid and ethylamine, followed by reaction with TMSCl using the methods of Example 9. m.p. 119–122° C.

EXAMPLE 11
N-Ethyl-3-(trimethylsilyl)-2-benzofurancarboxamide.

The title compound was obtained as a yellow solid in 5.2% overall yield from 2-benzofurancarboxylic acid and ethylamine, followed by reaction with TMSCl, using the methods of Example 9. m.p. 92–96° C.

EXAMPLE 12
N-Ethyl-2-(trimethylsilyl)-3-benzofurancarboxamide.

To a solution of benzofuran (25 g) in 50 mL carbon disulfide at –25° C. was added a solution of 35 g bromine in 50 mL carbon disulfide at between –20 and –10° C. and stirring was continued at –10° C. for 2 h. The precipitate was filtered and washed with hexane to give 43 g of 2,3-dibromo-2,3-dihydrobenzofuran as yellow solid.

To 11.3 g KOH (176 mmol) in 100 mL ethanol at 0° C. was added in small portions 22.2 g of 2,3-dibromo-2,3-dihydrobenzofuran, and the resulting reaction mixture was stirred at 0° C. for an additional 3 h. Most of the solvent was then removed in vacuo. Water and ether were added to the residue. The aq layer was separated and extracted with ether. The combined ether layers were washed with water and brine, dried ($MgSO_4$), and concentrated to give 17 g of 3-bromobenzofuran.

To a solution of 3-bromobenzofuran (10.5 g) in 120 mL ether at below –110° C. under a positive nitrogen atmosphere was added dropwise 2.5 M of n-BuLi in hexane (23 mL) at below –100° C., and stirring was continued at below –100° C. for 3 h. Solid carbon dioxide was added and the mixture was allowed to warm to 0° C. Water was added and the two layers were separated. The aq layer was acidified with conc HCl and extracted with methylene chloride. The methylene chloride solution was washed with brine, dried ($MgSO_4$), and concentrated to give 3 g of solid 3-benzofurancarboxylic acid.

To a solution of diisopropylamine (4 mL) in 20 mL THF at –60° C. was added 2.5 M of n-BuLi in hexane (17 mL), and the solution was stirred at between –20 and –60° C. for 1 h. To this, a solution of 3-benzofurancarboxylic acid (2.6 g) in 30 mL THF was added at <–70° C. After 1 h, TMSCl (7 mL) was added at <–70° C., and stirring was continued for an additional 1 h. The solution was allowed to warm to 0° C., quenched with 2 N HCl and extracted with methylene chloride. The organic solution was washed with brine, dried and concentrated to give 3.6 g of 2-(trimethylsilyl-3-benzofurancarboxylic acid.

A solution of this crude acid (0.6 g, 2.6 mmol) in 6 mL thionyl chloride, containing 6 drops of DMF was refluxed for 3 h, then cooled and concentrated in vacuo to give the crude acid chloride. A solution of the acid chloride in 6 mL methylene chloride was added to 6 mL of 70% aq ethylamine at –20° C. After 3 h at RT, water was added. The organic layer was separated, washed with brine, dried and concentrated in vacuo. The residue was purified by flash chromatography with 10% ethyl acetate-hexane to give 0.4 g of the product as a white solid, a yield of 58.9%. m.p. 141–144° C.

EXAMPLE 13
N-2-Propenyl-2-(trimethylsilyl)benzo[b]thiophene-3-carboxamide.

The title compound was prepared as a white solid in 26.1% yield from the product of example f using the method of Example 9. m.p. 72–75° C.

EXAMPLE 14
N,N-Diethyl-2-(trimethylsilyl)benzo[b]thiophene-3-carboxamide.

To a mixture of acids of example a (3.7 g) in 60 mL THF at –70° C. was added 2.5 M of n-BuLi in hexane (19 mL) at <–65° C. and stirring was continued at <–70° C. for 1.5 h. TMSCl (9 mL) was then added dropwise to the solution at <–70° C. After 1 h at <–70° C., the solution was warmed to 0° C. and poured into ice-water. Methylene chloride was added. The aq layer was separated and extracted with methylene chloride. The combined organic layers were washed with brine, dried, and concentrated in vacuo to give 4.5 g of solid. Trituration of the solid with 5% ethyl acetate-hexane gave 4.1 g of analytically pure 2-(trimethylsilyl)-3-benzothiophene-carboxylic acid.

The title compound was obtained as an orange oil in 82.2% yield from this acid and diethylamine using the method of Example b. $n_D^{26}$ 1.5683.

EXAMPLE 15
N-Ethyl-2-(trimethylsilyl)benzo[b]thiophene-3-carboxamide 1,1-dioxide.

A mixture of the product of Example 8 (0.6 g, 2.2 mmol) and 1 g of 80–85% 3-chloroperoxybenzoic acid in 16 mL methylene chloride was refluxed for 2 h, then cooled and diluted with additional methylene chloride. The solution was treated sequentially with sat sodium metabisulfite, 1.25N NaOH, and brine; then dried and concentrated in vacuo. Flash chromatography of the residue with 35% ethyl acetate-hexane gave 0.5 g of the desired product as a white solid, a yield of 74.5%. m.p. 135–148° C.

EXAMPLE 16
N-Ethyl-N-(methylthio)-2-(trimethylsilyl)benzo[b]-thiophene-3-carboxamide.

To a solution of the product of Example 8 (1.1 g, 4 mmol) in 20 mL THF at <−60° C. under a positive nitrogen atmosphere was added dropwise 2.5M of n-BuLi in hexane (2.2 mL) at <−60° C., and the solution was stirred for 0.5 h. A solution of methyl methanethiolsulfonate (0.6 g, 4.8 mmol) in 2 mL THF was added at <−60° C. After 1 h at ambient temperature, the solution was poured into ice water and extracted with methylene chloride. The organic layer was washed with brine, dried, and concentrated in vacuo. The residue was purified on a silica gel column using 8% ethyl acetate-hexane to give 1 g of the desired product as a viscous yellow oil, a yield of 76.9%. $n_D^{24}$ 1.5886.

EXAMPLE 17
N-Hydroxy-N-(1-methylethyl)-2-(trimethylsilyl)benzo[b]-thiophene-3-carboxamide.

A mixture of 2-(trimethylsilyl)-3-benzothiophenecarboxylic acid (0.8 g, 3.2 mmol), made as in Example 14, and thionyl chloride (6 mL) was refluxed for 2 h. The excess thionyl chloride was removed under reduced pressure. The crude acid chloride was dissolved in 20 mL methylene chloride and added to a mixture of N-isopropylhydroxylamine hydrochloride (0.4 g, 3.6 mmol) and 4 g sodium bicarbonate in 20 mL methylene chloride and 20 mL water at 0° C. The resulting mixture was stirred at RT for 2 h. The organic layer was separated, washed with brine, dried, and concentrated in vacuo. The crude product was chromatographed on a silica gel column with 10% ethyl acetate/hexane to give 0.65 g of the title compound as a yellow solid, a 66.1% yield. m.p. 115–118° C.

The following compounds were prepared using Methods D and E.

| EX. NO. | COMPOUND | M.P. |
| --- | --- | --- |
| 18 | N-(2-bromoethyl) 2-[(1,1-dimethyl ethyl)amino]-1-naphthamide | 203° C. dec |
| 19 | N-(2-bromoethyl) 2-[(1,1-dimthyl propyl)amino]-1-naphthamide | 151–153° C. |

The following compounds were prepared using Method F.

| EX. NO. | COMPOUND | M.P. |
| --- | --- | --- |
| 20 | N-ethyl 2-[(1,1-dimethyl ethyl)amino]-1-naphthamide | 149–150° C. |
| 21 | N-propyl 2-[(1,1-dimethyl ethyl)amino]-1-naphthamide | 142–143° C. |

The following compounds were prepared using Method G.

| EX. NO. | COMPOUND | M.P. |
| --- | --- | --- |
| 22 | N-ethyl 2-[(1,1-dimethyl propyl)amino]-1-naphthamide | 126–129° C. |
| 23 | N-ethyl 2-[(1,1-diethyl ethyl)amino]-1-naphthamide | 101–104° C. |

The following compounds were prepared using Method H.

| EX. NO. | COMPOUND | M.P. |
| --- | --- | --- |
| 24 | N-propyl 2-[(1,1-diethyl ethyl)amino]-1-naphthamide | 93–96° C. |
| 25 | N-propyl 2-[(1,1-dimethyl propyl)amino]-1-naphthamide | 104–107° C. |

The following compounds were prepared using Method J or

| EX. NO. | COMPOUND | METHOD | M.P. |
| --- | --- | --- | --- |
| 26 | N-ethyl 2-[(1,1-dimethyl propyl)oxy]-1-naphthamide | J | 91–93° C. |
| 27 | N-allyl 2-[(1,1-dimethyl propyl)oxy]-1-naphthamide | J | 79–81° C. |
| 28 | N-ethyl 2-[(1,1-diethyl ethyl)oxy]-1-naphthamide | K | 85–86° C. |
| 29 | N-allyl 2-[(1,1-diethyl ethyl)oxy]-1-naphthamide | K | 70–72° C. |
| 30 | N,N-diethyl 2-[(1,1-diethyl ethyl)oxy]-1-naphthamide | J | Oil |
| 31 | N-propyl 2-[(1,1-diethyl ethyl)oxy]-1-naphthamide | K | 85–86° C. |
| 32 | N-ethyl 2-[(1,1-diethyl propyl)oxy]-1-naphthamide | K | 105–106° C. |
| 33 | N-allyl 2-[(1,1-diethyl propyl)oxy]-1-naphthamide | K | 78–79° C. |
| 34 | N-propyl 2-[(1,1-diethyl propyl)oxy]-1-naphthamide | J | 101–102° C. |
| 35 | N,N-dipropyl 2-[(1,1-diethyl propyl)oxy]-1-naphthamide | J | oil |
| 36 | N-ethyl 2-[(1-methyl-1-cyclopentyl)oxy]-1-naphthamide | J | 93–94° C. |
| 37 | N-allyl 2-[(1-methyl-1-cyclopentyl)oxy]-1-naphthamide | J | 94–96° C. |
| 38 | N-ethyl 2-[(1-methyl-1-cyclohexyl)oxy]-1-naphthamide | K | 123–124° C. |
| 39 | N-allyl 2-[(1-methyl-1-cyclohexyl)oxy]-1-naphthamide | K | 91–94° C. |
| 40 | N-propyl 2-[(1-methyl-1-cyclohexyl)oxy]-1-naphthamide | K | 83–84° C. |

The following compounds were prepared using Method L.

| EX. NO. | COMPOUND | M.P. |
| --- | --- | --- |
| 41 | N-ethyl 5-trimethylsilyl benzothiophene-4-carboxamide | 153–155° C. |
| 42 | N-ethyl 5-trimethylsilyl benzofuran-4-carboxamide | 102–104° C. |

-continued

| EX. NO. | COMPOUND | M.P. |
|---|---|---|
| 43 | N-ethyl 6-trimethylsilyl benzothiophene-7-carboxamide | 130–134° C. |
| 44 | N-ethyl 6-trimethylsilyl benzofuran-7-carboxamide | 108–109° C. |

OTHER COMPOUNDS

Compounds in which the X of —C(X)amine is S may be prepared by mixing the corresponding oxyamide with Lawesson's reagent in xylene and refluxing overnight. The mixture is then cooled and filtered. The filtrate is partitioned between ether and water; the organic layer is washed with 10% HCl, dried (MgSO$_4$), and concentrated. The crude product may be purified by chromatography.

Compounds in which W is —CH$_2$— and Q is Si are prepared by introducing the methyl group ortho to the amide by using any one of General Methods A, B, or C. The resulting compound is worked up in the usual manner and purified by chromatography. It is then reacted with TMSCl using one of General Methods A, B, or C. The desired product is worked up in the usual manner and purified by chromatography.

BIOLOGICAL ASSAYS

The compounds prepared in the above examples have demonstrated control of Ggt in one or more of the following test methods. The results are shown in the table below.

In vitro Assay

The test compounds (0.25 mL of an appropriate stock solution in acetone) are incorporated into 25 mL minimal media agar [prepared by autoclaving a solution of 17.5 g Czapek Dox broth (Difco), 7.5 g purified agar or Bactoagar (Difco), and 500 mL distilled/deionized water, and then adding 50 μL of 1 mg/mL thiamine hydrochloride and 50 μL of 1 mg/mL biotin in 5% ethanol] and plates are prepared.

Each plate is inoculated by placing in a triangular shape three 4-mm plugs of *Gaeumannomyces graminis* var. tritici (Ggt) grown on the minimal media agar described above. The plates are incubated in the dark at 19–20° C. for 4 to 5 days. The growth of the fungus is measured as the diameter of the mycelial growth. The result is expressed as Percent Inhibition, calculated as [1−[(mm growth on treated plate−4)/(mm growth on control plate −4)]]×100.

In vivo Assay

Compounds are tested for control of Ggt on 'Bergen' or 'Anza' varieties of wheat grown in 3-inch square pots containing soil infested with Ggt. The infestation is accomplished by mixing the soil with an inoculum prepared by growing Ggt on ¼ strength potato dextrose agar (4.875 g potato dextrose agar, 5.0 g Bacto agar, 500 mL distilled, deionized water) in plates and using plugs from the plates to infest sterile oats (400 cc whole oats, 350 mL deionized water, autoclaved). After a onemonth incubation period at room temperature, the oats are dried and mixed with the soil at 4% v/v. Four wheat seeds are placed on top of the soil in each pot. The test compounds are prepared as an 1:9 acetone/water v/v solution containing 0.18% Tween® 20 to provide a treatment rate of 0.5 and/or 0.1 mg active ingredient per pot, treated with 3 mL test solution per pot. Five pots are used for each treatment level and the controls, which are untreated, inoculated and non-inoculated pots. After one hour drying time, the seeds are covered with more of the appropriate soil and a layer of vermiculite. The pots are placed in a growth chamber and watered each day. After four weeks, each pot is evaluated for evidence of disease by examination of the seminal roots of each plant under a dissecting microscope. A 0 to 5 rating scale having the following meanings is used:

0=no runner hyphae or lesions present

1=runner hyphae and a few small lesions present on <10% of root system

2=runner hyphae and small lesions present on 10–25% of root system

3=runner hyphae and lesions present on 25–50% of root system

4=runner hyphae and many, large, coalescing lesions on >50% of root system

5=root system and culm completely inundated with lesions and runner hyphae

From each set of five replicates a high or low score may be eliminated to assure the best representative scores are used to calculate a replicate mean by averaging the remaining scores. This mean score is then compared to the untreated control score and a percent disease control is calculated.

The results of these in vitro and in vivo tests are reported in the Table below. If the calculation resulted in "0" or less, as compared to the untreated control, a "N" is shown to indicate no control.

| | Test Results I | | | | | |
|---|---|---|---|---|---|---|
| | In vitro (ppm) | | | In vivo (ppm) | | |
| EX. NO. | 10 | 1 | 0.1 | 0.5 | 0.1 | 0.02 mg/pot |
| 1 | 79 | 79 | 0 | — | 18 | |
| 2 | 100 | 46 | 15 | N | N | |
| 3 | 100 | 0 | 0 | 68 | — | |
| 4 | 100 | 100 | 100 | 99 | 85 | |
| 5 | 100 | 94 | 0 | 27 | 18 | |
| 6 | 93 | 86 | 21 | — | 53 | |
| 7 | 100 | 100 | 88 | 79 | 40 | |
| 8 | 100 | 93 | 97 | 71 | 43 | |
| 9 | 88 | 0 | 0 | — | N | |
| 10 | 85 | 80 | 13 | — | — | |
| 11 | 82 | 42 | 27 | — | — | |
| 12 | 100 | 97 | 97 | 97 | 85 | |
| 13 | 100 | 100 | 100 | 94 | 84 | |
| 14 | 100 | 92 | 42 | 94 | 76 | |
| 15 | 83 | 30 | 10 | — | — | |
| 16 | 100 | 100 | 100 | 93 | 87 | |
| 17 | 100 | 100 | 96 | 46 | 42 | |
| 18 | 98 | 88 | 10 | 14 | 0 | 0 |
| 19 | 98 | 93 | 68 | 22 | 0 | 0 |
| 20 | 100 | 98 | 80 | 61 | 24 | 5 |
| 21 | 97 | 97 | 95 | 78 | 60 | 35 |
| 22 | 98 | 98 | 95 | 70 | 41 | 11 |
| 23 | 43 | 21 | 21 | 85 | 65 | 50 |
| 24 | 100 | 95 | 95 | 76 | 38 | 32 |
| 25 | 100 | 100 | 95 | 78 | 57 | 17 |
| 26 | 98 | 95 | 76 | 84 | 56 | 17 |
| 27 | 98 | 98 | 93 | 95 | 75 | 27 |
| 28 | 96 | 96 | 74 | 78 | 40 | 19 |
| 29 | 96 | 96 | 96 | 75 | 57 | 40 |
| 30 | 96 | 96 | 91 | 28 | 43 | 31 |
| 31 | 98 | 17 | 7 | 3 | 0 | 0 |
| 32 | 97 | 97 | 87 | 58 | 35 | 15 |
| 33 | 100 | 100 | 97 | 59 | 45 | 19 |
| 34 | 95 | 95 | 95 | 49 | 44 | 18 |
| 35 | 95 | 19 | 0 | 1 | 0 | 0 |
| 36 | 100 | 98 | 76 | 60 | 0 | 0 |
| 37 | 98 | 98 | 93 | 63 | 53 | 28 |
| 38 | 30 | 43 | 0 | | No Data* | |
| 39 | 96 | 96 | 57 | 28 | 11 | 0 |
| 40 | 98 | 83 | 74 | 60 | 32 | 3 |

-continued

Test Results I

| | In vitro (ppm) | | | In vivo (ppm) | | |
|---|---|---|---|---|---|---|
| EX. NO. | 10 | 1 | 0.1 | 0.5 | 0.1 | 0.02 mg/pot |
| 41 | 100 | 98 | 98 | 100 | 99 | 75 |
| 42 | 100 | 98 | 90 | 91 | 87 | 68 |
| 43 | 100 | 100 | 98 | 88 | 79 | 50 |
| 44 | 100 | 98 | 98 | | No Data** | |

*Insufficient in vitro activity to warrant secondary testing.
**Not tested.

Test Results II

| EX. NO. | IN VITRO (IC50*) |
|---|---|
| 24 | 0.000814 |
| 25 | 0.001000 |
| 23 | 0.006625 |
| 21 | 0.008500 |
| 22 | 0.009182 |
| 20 | 0.071644 |
| 33 | 0.006473 |
| 34 | 0.006625 |
| 37 | 0.007429 |
| 30 | 0.007429 |
| 29 | 0.008143 |
| 27 | 0.008435 |
| 32 | 0.042239 |
| 40 | 0.063571 |

*IC50 is determined as follows:

To determine $IC_{50}$ values, an in vitro assay was run on each compound at the concentrations of 1, 0.1, 0.01, 0.001, and 0.0001 ppm. The percent inhibition was calculated for each concentration using the equation described in the in vitro assay under the section on Biological Assays. Using the two ordered pairs of (concentration, % inhibition) that bracket 50% inhibition of fungal growth, the concentration for 50% inhibition is calculated from the following equation. $IC_{50} = [(50-I_2)C_1 + (I_1-50)C_2]/(I_1-I_2)$, where $C_1 = 10C_2$.

In vivo (8 week) Assay

An advanced 8-week seed treatment in vivo assay in soil is as follows.

In vivo Assay

Compounds are tested for control of Ggt on 'Bergen' or 'Anza' varieties of wheat grown in 6-inch round pots containing soil (equal to thirds of Metro-mix, sand, and silt-loam field soil, all steam sterilized). Seeds are treated with a solution of compound of the present invention at 10,000 ppm stock solution in acetone. 20 mg in 2 ml will treat 10 g of seed at each of 4 rates. Using a 10,000 ppm stock for each compound make the following dilutions series:

| | gai/100 kg composition | |
|---|---|---|
| 1 | 100 | 1 ml of stock |
| 2 | 50 | 1 ml stock + 1 ml acetone |
| 3 | 25 | 1 ml #2 + 1 ml acetone |
| 4 | 12.5 | 1 ml #3 + 1 ml acetone (discard 1 ml or proceed) |
| 5 | 6.25 | 1 ml #4 + 1 ml acetone (discard 1 ml) |

(5 is optional and not used in all tests)
*each vial of solution should contain 1 ml to treat 10 g of seed. 10 g packets of wheat seed (variety 'Bergen'), one for each treatment are prepared.

A treatment jar is rinsed 2 times with 3 ml of actone. Then 1 ml of the solution is swirled to cover the base of the jar. 10 g of seed are added to the jar and capped after which the jar is swirled and shaken until the seeds get a rapid and even coverage. After about 30–50 seconds the lid is removed as the shaking is continued. After 1 minute the jar is set down to dry. When dry, the seed are poured back into the envelope for either planting in the pots or stored until such planting. The method of planting is as follows:

LARGE POT GREENHOUSE TAKE-ALL ASSAY

The 6-inch pots are packed to their ledge with the above soil mix. Method:
a) Treated seed is placed on the surface of the soil (packed to ledge) at the rate of 8 seeds per pot with the seeds about 2–3 inches apart. 5 pots (replicates) are planted per treatment.
b) 15 ml of oat inoculum (about 4g) are measured and sprinkled evenly over the soil surface of each pot.
c) The soil/seed/inoculum is covered with 180 ml of soil mix (same as above). A 150 ml beaker filled to the top edge is about 180 ml.
d) Initially each of the prepared pots is watered lightly several times to wet soil without washing out seeds.
e) In cool winter months the prepared pots are left in the greenhouse at 16–18° C. with only minimal supplemental light. In warmer months the prepared pots are put in a growth chamber set at 17° C. for 3–4 weeks to establish disease, then placed in a greenhouse until harvest. The wheat is harvested, washed, and the roots are rated after 7–10 weeks.
f) A % of diseased root area is assigned values using 1, 5, 10, 20, 30, 40, 50, 60, 80, or 100%. Each pot of plants gets a single rating.

Test Results III

| | % control (rates are g/kg seed) | | | | |
|---|---|---|---|---|---|
| EX. NO. | 1 g | 0.5 | 0.25 | 0.125 | non-treated test# |
| 26 | 25 | 4 | 25 | 25 | 48 32 |
| 27 | 25 | 0 | 21 | 21 | 48 32 |
| 37 | 4 | 4 | 4 | 4 | 48 33 |
| 34 | 9 | 0 | 17 | | 46 38 |
| 30 | 13 | 0 | 22 | | 46 38 |
| 29 | 4 | 4 | 0 | | 46 38 |
| 40 | 22 | 13 | 13 | | 46 38 |

FIELD TESTS

The compounds of Examples 1–44 are combined with various adjuvants, carriers, and other additives and mixed with wheat and barley seed at rates of from 0.01 to 50 g active ingredient per kg of seed which reduce the incidence of Gg in previously infested fields compared to check fields seeded with untreated seed.

COMPOSITION EXAMPLES

| | Wt. Pct. |
|---|---|
| Suspension Concentrate: | |
| Compound No. 21 | 48.900 |
| Polyoxypropylene-polyoxyethylene block copolymer | 2.550 |
| Sodium Lignin Sulfonate | 2.040 |
| 10% Dimethylpolysiloxane Emulsion | 1.020 |
| 1% Xanthan gum solution | 0.990 |
| Water | 43.250 |
| Emulsifiable Concentrate: | |
| Compound No. 23 | 13.5 |
| Ethoxylated sorbitan (20EO) | 5.0 |
| C9 Aromatics | 81.5 |
| Wettable Powder: | |
| Compound No. 41 | 75.0 |
| Sodium lignin sulfonate | 3.0 |
| Sodium N-methyl-N-oleyl-taurate | 1.0 |
| Kaolinite clay | 11.0 |
| Granule: | |
| Compound No. 42 | 1.0 |
| Propylene glycol | 5.0 |
| Montmorillonite (24/48 mesh) | 94.0 |
| Dust: | |
| Compound No. 43 | 50.0 |
| Graphite | 10.0 |
| Kaolinite clay | 40.0 |

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth is to be interpreted as illustrative and not in a limiting sense.

What is claimed is:

1. A method of controlling disease in a plant caused by Gaeumannomyces sp. in said plant comprising applying to the seed or the soil of said plant a fungicidally effective amount of a fungicide of the formula a)

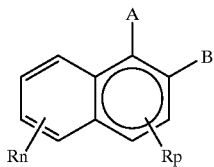

b)

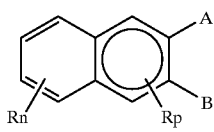

c)

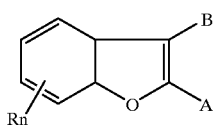

d)

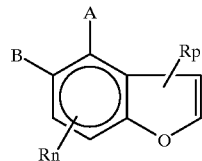

e)

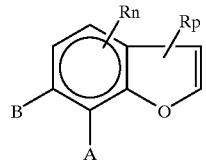

f)

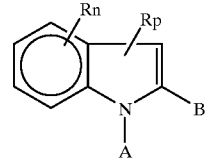

g)

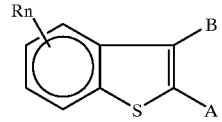

h)

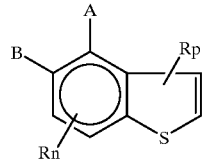

i)

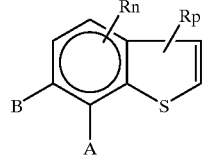

j)

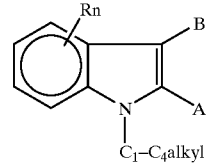

A is —C(X)-amine; B is —$W_m$—Q($R_2$)$_3$; and A can be B when B is A except when the formula is f), then Q cannot be Si;

Q is C or Si;

W is —NH—, —O— or —NCH$_3$—;

X is O or S;

m is 0 or 1 provided that m is 0 when Q is Si;

n is 0, 1, 2, or 3;

p is 0, 1 or 2; and n plus p is equal to or less than 3;

each R is independently selected from
   a) halo, formyl, cyano, amino, nitro, thiocyanato, isothiocyanato, trimethylsilyl, and hydroxy;
   b) $C_1$–$C_4$ alkyl, alkenyl, alkynyl, $C_3$–$C_6$ cycloalkyl, and cycloalkenyl, each optionally substituted with halo, hydroxy, thio, amino, nitro, cyano, formyl, phenyl, $C_1$–$C_4$ alkoxy, alkylcarbonyl, alkylthio, alkylamino, dialkylamino, alkoxycarbonyl, (alkylthio)carbonyl, alkylaminocarbonyl, dialkylaminocarbonyl, alkylsulfinyl, or alkylsulfonyl;

c) phenyl, furyl, thienyl, pyrrolyl, each optionally substituted with halo, formyl, cyano, amino, nitro, $C_1$–$C_4$ alkyl, alkenyl, alkynyl, alkoxy, alkylthio, alkylamino, dialkylamino, haloalkyl, and haloalkenyl;

d) $C_1$–$C_4$ alkoxy, alkenoxy, alkynoxy, $C_3$–$C_6$ cycloalkyloxy, cycloalkenyloxy, alkylthio, alkylsulfinyl, alkylsulfonyl, alkylamino, dialkylamino, alkylcarbonylamino, aminocarbonyl, alkylaminocarbonyl, dialkylaminocarbonyl, alkylcarbonyl, alkylcarbonyloxy, alkoxycarbonyl, (alkylthio)carbonyl, phenylcarbonylamino, phenylamino, each optionally substituted with halo;

each $R_2$ is independently selected from alkyl, alkenyl, alkynyl, cycloalkyl, cycloalkenyl and phenyl, each optionally substituted with $R_4$ or halogen; and wherein, when Q is C, $R_2$ may also be selected from halo, alkoxy, alkylthio, alkylamino, and dialkylamino;

wherein two $R_2$ groups may be combined to form a cyclo group with Q;

R4 is $C_1$–$C_4$ alkyl, haloalkyl, alkoxy, alkylthio, alkylarmino, or dialkylamino;

or an agronomic salt thereof.

2. The method of claim 1 wherein the formula is a), b), g), h) or i).

3. The method of claim 2 wherein A is —C(O)-amine, wherein the amino radical is substituted with one or two groups selected from hydroxy; alkyl, alkenyl, and alkynyl, which may be straight or branched chain or cyclic; alkoxyalkyl; haloalkyl; hydroxyalkyl; alkylthio; alkylthioalkyl; alkylcarbonyl; alkoxycarbonyl; aminocarbonyl; alkylaminocarbonyl; cyanoalkyl; mono- or dialkylamino; phenyl, phenylalkyl or phenylalkenyl, each optionally substituted with one or more $C_1$–$C_4$ alkyl, alkoxy, haloalkyl, $C_3$–$C_6$ cycloalkyl, halo, or nitro groups; and $C_1$–$C_4$ alkyl or alkenyl substituted with pyridinyl, thienyl, or furanyl; and wherein the amino radical may be a N-bonded heterocycle selected from morpholine, piperazine, piperidine, pyrrole, pyrrolidine, imidazole, and triazoles, each optionally substituted with $C_1$–$C_6$ alkyl groups.

4. The method of claim 3 wherein the amino radical is substituted with one or more groups selected from alkyl, alkenyl, alkynyl, which may be straight or branched; haloalkyl; and alkylthioalkyl.

5. The method of claim 4 wherein m is zero.

6. The method of claim 4 wherein A is ethylaminocarbonyl, propylaminocarbonyl or allylaminocarbonyl.

7. The method of claim 6 wherein A is allylaminocarbonyl.

8. The method of claim 5 wherein Q is Si.

9. The method claim 8 wherein $R_2$ is $C_1$–$C_4$ alkyl or haloalkyl.

10. The method of claim 9 wherein $R_2$ is methyl.

11. The method of claim 5 wherein Q is C.

12. The method of claim 11 wherein $R_2$ is $C_1$–$C_4$ alkyl or haloalkyl or two $R_2$ are combined with Q to form $C_3$–$C_6$ cycloalkyl.

13. The method of claim 11 wherein B is independently selected from 1,1-dimethylpropyl, 1,1-diethylethyl or 1-methyl-1-cyclopentyl.

14. The method of claim 4 wherein m is 1 and Q is C.

15. The method of claim 14 wherein W is O.

16. The method of claim 15 wherein $R_2$ is $C_1$–$C_4$ alkyl or haloalkyl or two $R_2$ are combined with Q to form $C_3$–$C_6$ cycloalkyl.

17. The method of claim 15 wherein B is 1,1-dimethylpropyloxy,1,1-diethylethyloxy, or 1-methyl-1-cyclopentyloxy.

18. The method of claim 14 wherein W is NH or $NCH_3$.

19. The method of claim 18 wherein $R_2$ is $C_1$–$C_4$ alkyl or haloalkyl or two $R_2$ are combined with Q to form $C_3$–$C_6$ cycloalkyl.

20. The method of claim 4 wherein $R_n$ and $R_p$ are independently selected from halogen or lower alkyl.

21. A fungicidal composition for use in the method of claim 1 comprising an adjuvant and an amount of a compound described therein which is effective to control Take-all.

22. A compound of the formula

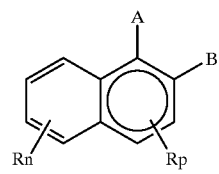

a)

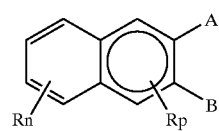

b)

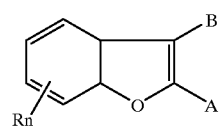

c)

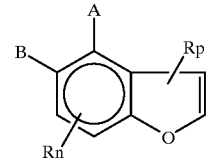

d)

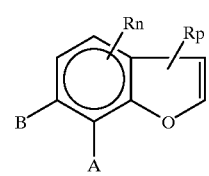

e)

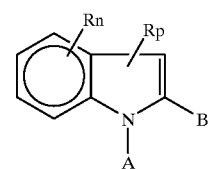

f)

-continued

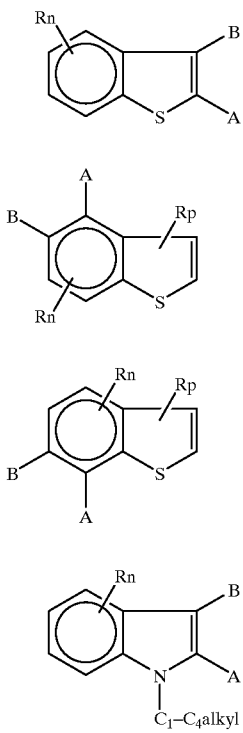

g)

h)

i)

j)

A is —C(X)-amine; B is —W$_m$—Q(R$_2$)$_3$; and A can be B when B is A except when the formula is f), Q cannot be Si;
Q is C or Si;
W is —NH—, —NCH$_3$— or —O—;
X is O or S;
m is 0 or 1, provided that m is 0 when Q is Si;
n is 0, 1, 2, or 3;
p is 0, 1 or 2; and n plus p is equal to or less than 3;
each R is independently selected from
 a) halo, formyl, cyano, amino, nitro, thiocyanato, isothiocyanato, trimethylsilyl, and hydroxy;
 b) C$_1$–C$_4$ alkyl, alkenyl, alkynyl, C$_3$–C$_6$ cycloalkyl, and cycloalkenyl, each optionally substituted with halo, hydroxy, thio, amino, nitro, cyano, formyl, phenyl, C$_1$–C$_4$ alkoxy, alkylcarbonyl, alkylthio, alkylamino, dialkylamino, alkoxycarbonyl, (alkylthio)carbonyl, alkylaminocarbonyl, dialkylaminocarbonyl, alkylsulfinyl, or alkylsulfonyl;
 c) phenyl, furyl, thienyl, pyrrolyl, each optionally substituted with halo, formyl, cyano, amino, nitro, C$_1$–C$_4$ alkyl, alkenyl, alkynyl, alkoxy, alkylthio, alkylamino, dialkylamino, haloalkyl, and haloalkenyl;
 d) C$_1$–C$_4$ alkoxy, alkenoxy, alkynoxy, C$_3$–C$_6$ cycloalkyloxy, cycloalkenyloxy, alkylthio, alkylsulfinyl, alkylsulfonyl, alkylamino, dialkylamino, alkylcarbonylamino, aminocarbonyl, alkylaminocarbonyl, dialkylaminocarbonyl, alkylcarbonyl, alkylcarbonyloxy, alkoxycarbonyl, (alkylthio)carbonyl, phenylcarbonylamino, phenylamino, each optionally substituted with halo;
each R$_2$ is independently selected from alkyl, alkenyl, alkynyl, cycloalkyl, cycloalkenyl and phenyl, each optionally substituted with R4 or halogen; and wherein, when Q is C, R$_2$ may also be selected from halo, alkoxy, alkylthio, alkylamino, and dialkylamino;
wherein two R$_2$ groups may be combined to form a cyclo group with Q;
R$_4$ is C$_1$–C$_4$ alkyl, haloalkyl, alkoxy, alkylthio, alkylamino, or dialkylamino; provided that for formula a), when A is 1-phenylaminocarbonyl, B is not trifluoromethyl, for formula b), when A is 2-diethylaminocarbonyl, B is not trimethylsilyl, and for formula f), when A is N-t-butylaminocarbonyl, B is not trimethylsilyl, and when A is N-diethylaminocarbonyl, B is not either 2-methyl- 1,3-dithian-2-yl or 2-ethyl-1,3-dithian-2-yl;
or an agronomic salt thereof.

23. The compound of claim 22 wherein the formula is a), b), g), h) or i).

24. The compound of claim 23 wherein A is —C(O)-amine, wherein the amino radical is substituted with one or two groups selected from hydroxy; alkyl, alkenyl, and alkynyl, which may be straight or branched chain or cyclic; alkoxyalkyl; haloalkyl; hydroxyalkyl; alkylthio; alkylthioalkyl; alkylcarbonyl; alkoxycarbonyl; aminocarbonyl; alkylaminocarbonyl; cyanoalkyl; mono- or dialkylamino; phenyl, phenylalkyl or phenylalkenyl, each optionally substituted with one or more C$_1$–C$_4$ alkyl, alkoxy, haloalkyl, C$_3$–C$_6$ cycloalkyl, halo, or nitro groups; and C$_1$–C$_4$ alkyl or alkenyl substituted with pyridinyl, thienyl, or furanyl; and wherein the amino radical may be a N-bonded heterocycle selected from morpholine, piperazine, piperidine, pyrrole, pyrrolidine, imidazole, and triazoles, each optionally substituted with C$_1$–C$_6$ alkyl groups.

25. The method of claim 18 wherein B is 1,1-dimethylpropylamino,1,1-dimethylethylamino, or 1-methyl-1-cyclopentylamino.

26. The compound of claim 24 wherein the amino radical is substituted with one or more groups selected from alkyl, alkenyl, alkynyl, which may be straight or branched; haloalkyl; and alkylthioalkyl.

27. The compound of claim 26 wherein A is ethylaminocarbonyl, propylaminocarbonyl or allylaminocarbonyl.

28. The compound of claim 27 wherein A is allylaminocarbonyl.

29. The compound of claim 26 wherein m is zero.

30. The compound of claim 29 wherein Q is Si.

31. The compound claim 30 wherein R$_2$ is C$_1$–C$_4$ alkyl or haloalkyl.

32. The compound of claim 31 wherein R$_2$ is methyl.

33. The compound of claim 29 wherein Q is C.

34. The compound of claim 33 wherein R$_2$ is C$_1$–C$_4$ alkyl or haloalkyl or two R$_2$ are combined with Q to form C$_3$–C$_6$ cycloalkyl.

35. The compound of claim 33 wherein B is independently selected from 1,1-dimethylpropyl, 1,1-diethylethyl, or 1-methyl-1-cyclopentyl.

36. The compound of claim 26 wherein m is 1 and Q is C.

37. The compound of claim 36 wherein W is O.

38. The compound of claim 37 wherein R$_2$ is C$_1$–C$_4$ alkyl or haloalkyl or two R$_2$ are combined with Q to form C$_3$–C$_6$ cycloalkyl.

39. The compound of claim 37 wherein B is 1,1-dimethylpropyloxy,1,1-diethylethyloxy, or 1-methyl-1-cyclopentyloxy.

40. The compound of claim 36 wherein W is NH or NCH$_3$.

41. The compound of claim 40 wherein R$_2$ is C$_1$–C$_4$ alkyl or haloalkyl or two R$_2$ are combined with Q to form C$_3$–C$_6$ cycloalkyl.

42. The compound of claim 40 wherein B is 1,1-dimethylpropylamino,1,1-dimethylethylamino, or 1-methyl-1-cyclopentylamino.

43. The compound of claim 26 wherein R$_n$ and R$_p$ are independently selected from halogen or lower alkyl.

* * * * *

UNITED STATES PATENT AND TRADEMARK OFFICE
CERTIFICATE OF CORRECTION

PATENT NO.: 5,994,270
DATED: November 30, 1999
INVENTOR(S): Phillion et al.

It is certified that errors appear in the above-identified patent, and that said Letters Patent is hereby corrected as shown below.

Column 25, Claim 1, line 27, delete "R4" and insert --$R_4$--.

Column 25, Claim 1, line 28, delete "alkylarmino" and insert --alkylamino--.

Column 28, Claim 22, line 1, delete "R4" and insert --$R_4$--.

Signed and Sealed this

Twenty-third Day of May, 2000

*Attest:*

Q. TODD DICKINSON

*Attesting Officer*      *Director of Patents and Trademarks*